United States Patent

Syed et al.

[11] Patent Number: 5,756,077
[45] Date of Patent: May 26, 1998

[54] HAIR PROTECTANT COMPOSITION AND PROCESS FOR PRESERVING CHEMICALLY PROCESSED HAIR DURING SUBSEQUENT CHEMICAL PROCESSING

[75] Inventors: Ali N. Syed, Inverness; Wagdi W. Habib, Barrington, both of Ill.

[73] Assignee: Avlon Industries, Inc., Bedford Park, Ill.

[21] Appl. No.: 713,760

[22] Filed: Sep. 13, 1996

[51] Int. Cl.$^6$ .................................................. A61K 7/06
[52] U.S. Cl. .......................................... 424/70.13
[58] Field of Search ............................. 424/70.13

[56] References Cited

U.S. PATENT DOCUMENTS

| | | | |
|---|---|---|---|
| 3,790,664 | 2/1974 | Krochock et al. | 424/47 |
| 3,958,581 | 5/1976 | Abegg et al. | 132/7 |
| 4,362,528 | 12/1982 | Grollier et al. | 8/406 |
| 4,668,508 | 5/1987 | Grollier et al. | 424/70 |
| 5,068,101 | 11/1991 | Akhtar et al. | 424/71 |
| 5,148,822 | 9/1992 | Akhtar | 132/204 |
| 5,415,860 | 5/1995 | Beucherie et al. | 424/401 |
| 5,436,010 | 7/1995 | Lau et al. | 424/450 |
| 5,482,704 | 1/1996 | Sweger et al. | 424/70.13 |

*Primary Examiner*—Kimberly Jordan
*Attorney, Agent, or Firm*—Gardner, Carton & Douglas

[57] ABSTRACT

A method for protecting previously chemically processed hair fibers from damage during subsequent chemical processing comprising the steps of: (a) applying to the previously processed hair fibers a protectorant composition comprising (i) a sugar; a starch hydrolysate, sorbitol, glycerol, propylene glycol, or a polyol, and (ii) and at least one cationic or non-ionic polar polymer; and thereafter, (b) processing the hair fibers with the same chemical process previously used; and thereafter (c) rinsing the hair for a time sufficient to remove all chemicals from the hair. Also claimed is a composition for protecting previously chemically treated hair and a kit for processing previously processed hair using the compositions of the invention.

26 Claims, No Drawings

HAIR PROTECTANT COMPOSITION AND PROCESS FOR PRESERVING CHEMICALLY PROCESSED HAIR DURING SUBSEQUENT CHEMICAL PROCESSING

FIELD OF THE INVENTION

This invention relates generally to the chemical processing of hair fibers, and more particularly to a composition and process for chemically treating new hair growth and preserving hair which has been previously chemically treated.

BACKGROUND OF THE INVENTION

Human hair has a variety of textures, from fine to coarse, and from straight to curly. In today's society, the ability to alter or change the texture of one's hair through chemical processes is important to both men and women. Hair care products and chemical processes that can alter the texture of hair are in great demand. Among individuals with excessively curly hair, products and processes that straighten or "relax" hair are especially popular, for such products and processes increase the ease of combing, ease of styling, and thereby enhance hair manageability. Permanent waving compositions, dyes and bleaches for hair are also popular.

In order to achieve permanent relaxing, chemical relaxers are used. The most common relaxing agents are highly alkaline and may contain sodium hydroxide, guanidine hydroxide, lithium hydroxide, quaternary ammonium hydroxide, thioglycolate or potassium hydroxide. The use of such relaxers is well known in the art and has been described previously, particularly in *Ethnic Hair Care: History, Trends and Formulation*, A. N. Syed, *Cosmet. and Toil.*, 108; 99–107 (1993) and U.S. Pat. No. 5,304,370 to Hawkins, et al.. Hair fibers are comprised of keratin, which is in turn comprised of polypeptide chains bonded together by three types of bonds: cystine (or disulfide) bonds, hydrogen bonds, and salt linkages. The alkaline relaxer operates primarily on the cystine bonds. When the cystine bonds are exposed to an alkaline relaxer, they are cleaved and transformed into lanthionine bonds. The chemical term for the alkaline hair relaxing process is lanthionization.

In the conventional relaxing process, an alkaline relaxing cream is first applied to the hair for eighteen to twenty minutes. During this step, hair gradually becomes physically straighter. After the alkaline relaxing cream has been left on the hair for eighteen to twenty minutes, it is rinsed from the hair with water for one to three minutes. Directions for use of conventional relaxing systems stress the importance of ensuring that the alkaline relaxing cream is left on the hair for no longer than twenty minutes. It is taught that if the relaxing cream is left on the hair for longer than twenty minutes, the hair will be overprocessed, and excessively damaged.

Although the conventional relaxing process decreases the amount of curl in hair, it also damages hair and skin. The conventional process causes hair fibers longitudinally to split and break, leaving it coarse, brittle, and damaged. In addition, exposure of the scalp to the alkaline relaxer can cause skin irritation and the appearance of burns. The damage to the hair is permanent and cannot be corrected by applying conditioning agents to the hair subsequent to the relaxing process. Therefore, individuals wishing to straighten their hair using the conventional relaxing process must suffer the damaging structural effects of the process on their hair.

Current practice of professionals in beauty salons is to reprocess the new hair growth of individuals with previously processed hair every 6 to 8 weeks. This is done by a repeated application of the desired processing agents. In these processes, the processing agents not only contact the new hair growth, but generally also overlap with and cover either a portion or all of the hair that has been previously chemically treated.

In the case of relaxing, for curly-haired individuals desiring to have long, straight hair, assuming an average hair growth rate of one inch every two months, they would need to relax their new hair growth approximately every two months. The new growth, along with a portion of previously chemically treated hair adjacent to the new hair growth, would potentially have been in contact with relaxers at 18 to 20 minutes each time. Repeated exposure of previously chemically treated hair to relaxer compositions during the relaxation of new hair growth causes damage to the cuticles and cortex of the previously chemically treated hair, thereby causing excessive drying, splitting and breakage of the previously chemically treated hair which has repeatedly been exposed to the alkaline relaxing composition. Such damaged hair is highly susceptible to further damage from combing and routine washings.

Repeated coloring, bleaching and permanent waving similarly cause structural damage to the hair, and may cause irritation to the skin. Permanent coloring agents (called "oxidation dyes") contain hydrogen peroxide and strongly alkaline ingredients, such as ammonia, which are damaging to hair, particularly after repeated applications. Examples of compositions and processes for dyeing hair are disclosed in U.S. Pat. No. 4,362,528 to Grollier et al. and are incorporated herein by reference. Bleaching agents generally contain hydrogen peroxide, which can also be damaging to hair. Permanent waving compositions often contain strong reducing agents, such as thioglycollic acid, which also causes damage to hair.

Thus, the conventional processes and compositions known in the art for chemically treating hair which has been previously chemically treated suffer from the disadvantage of causing excessive damage to the previously chemically treated hair fibers, due to overlapping application of the processing compositions during each retouch application. There is a desire and long-standing need to overcome these disadvantages.

One possible approach to protecting previously relaxed hair during subsequent relaxing is to incorporate acidic compounds at a low pH range (1–2) to counteract the effect of the highly alkaline relaxers. However, the large amount of relaxer cream required to straighten the hair (6 oz. per application) is unable to be neutralized by a lesser amount (0.5–1.0 oz.) of the protective acidic composition; hence, the hair damage continues to occur. In addition, these strongly acidic compounds must be used carefully or damage to both the operator and the subject may occur. In addition, many of these compositions are petroleum based and not water soluble, and are thus very difficult to remove from the hair. The inventors are unaware of any commercially available compositions for protecting previously relaxed, permanent waved, colored or bleached hair during subsequent repeated processing.

Therefore, the need for an effective composition and method which protects previously chemically treated hair during subsequent processing, and which overcomes the deficiencies in the prior art, still exists.

Thus, it is an object of the invention to provide a method for protecting previously chemically processed hair from further damage during subsequent processing.

It is another object of the invention to provide a hair protectorant composition for use with the method of the invention.

It is yet another object of the invention to provide a kit for performing chemical processes on hair which has been at least partially previously processed.

It is also an object of this invention to provide a method and a protectorant composition for relaxing hair which has been at least partially relaxed previously.

SUMMARY OF THE INVENTION

The invention is directed to a composition for use on hair which protects previously chemically treated hair during further processing. The composition comprises at least one of a sugar, a starch hydrolysate, sorbitol, glycerol, propylene glycol or a polyol; and at least one cationic or highly polar non-ionic polymer. The invention may optionally contain at least one quaternary ammonium compound. The invention is also directed to methods for chemically treating hair while preserving previously chemically treated hair, comprising the steps of applying the composition of the invention to the previously treated hair, chemically treating the hair with the same process as was used on the previously chemically treated hair, then rinsing the hair. Also claimed are kits for chemically processing hair while protecting previously processed hair comprising single-use portions of the desired processing composition and the composition of the invention, which may optionally include at least one of the following components: pre-processing conditioner, post-processing conditioner, gloves, cotton, a hair cap, shampoo and an applicator.

DETAILED DESCRIPTION

The compositions according to the invention comprise a sugar, a starch hydrolysate, sorbitol, glycerol, propylene glycol or a polyol in association with a cationic or highly polar non-ionic polymer in a cosmetically acceptable medium. Such media may include, but are not limited to, liquids, sprays, gels, cremes, emulsions and lotions. The composition may also comprise one or more of the following: quaternary ammonium compounds, pH adjusting agents, conditioning agents, colorants, gelling agents, preservatives, proteins and fragrance. The kits of the invention include a single-use application of the protectorant composition of the invention as well as a single-use application of any commercially available hair processing composition, and may optionally include gloves, at least one conditioner, an applicator, a hair cap and a shampoo, of which the conditioner and shampoo may be formulated specifically for the processing composition. It is intended that the hair processing composition includes, but is not limited to, coloring compositions, bleaching compositions and permanent waving compositions.

The sugars which can be used according to the invention are mono-, di- and polysaccharides. Sucrose, fructose, glucose and lactose are particularly suitable for use in the compositions of the present invention.

Representative examples of starch hydrolysates include, but are not limited to, Hystar CG, Hystar 6075, Hystar HM 75 and Hystar 7000, all of which may be obtained from Lonza, Inc., Fairlawn, N.J.

The cationic or non-ionic polar polymers which can be used in the invention are any polymers that are effective in attracting the sugar, starch hydrolysate, sorbitol, glycerol, propylene glycol or polyol to the hair and include, but are not limited to:

(a) cationic polyquaternary polymers that are the product of a condensation reaction of a lower dialklylamine ($C_1$–$C_3$), a difunctional epoxy compound and a third reactant selected from the group consisting of ammonia, primary amines, alkylene diamines having two to six carbon atoms, and polyamines, for example, the polymer that is the product of a condensation reaction of ethylenediamine, dimethylamine and epichlorohydrin (commercially available under the trade name Betz® 1195, Betz Laboratories, Trevose, Pa.);

(b) polyquaternium polymers, for example, polyquaternium-10 (commercially available under the trade name UCARE Polymer JR-30M from Amerchol Corporation, 136 Talmadge Rd., Edison, N.J.), and polyquaternium-4;

(c) Vinylpyrrolidone/dialkylaminoalkyl acrylate or methacrylate copolymers (quaternized or unquaternized), such as those sold under the name GAFQUAT (available from International Specialty Products, Boundbrook, N.J.), for example "copolymer 845" and "GAFQUAT 734 or 755," described in greater detail in particular in French Pat. No.'s 2,077,143 and 2,393,573, incorporated herein by reference;

(d) cationic polysaccharides such as those described in U.S. Pat. Nos. 3,589,978 and 4,031,307 which are incorporated herein by reference, and in particular Jaguar C 13 S sold by Meyhall;

(e) cationic polymers chosen from the group comprising:

(i) polymers containing units of the formula: —A—Z—A—Z—(I), in which A denotes a radical containing two amine groups, preferably a piperazinyl radical, and Z denotes a symbol B or B'; B and B', which are identical or different, denote a divalent radical which is a straight-chain or branched-chain alkylene radical which contains up to 7 consecutive carbon atoms in the main chain, which is unsubstituted or substituted by hydroxyl groups and which can also contain oxygen, nitrogen and sulphur atoms and 1 to 3 aromatic and/or heterocyclic rings, the oxygen, nitrogen and sulphur atoms being present in the form of ether or thioether, sulphoxide, sulphone, sulphonium, amine, alkylamine, alkenylamine, benzylamine, amine oxide, quaternary ammonium, amide, imide, alcohol, ester and/or urethane groups; these polymers are described in French Pat. No. 2,162,025, incorporated herein by reference;

(ii) polymers containing units of the formula: —A—$Z_1$—A—$Z_1$—(II), in which A denotes a radical containing two amine groups, preferably a piperazinly radical, and $Z_1$ denotes the symbol $B_1$ or $B'_1$ and denotes the symbol $B'_1$ least once; $B_1$ denotes a divalent radical which is a straight-chain or branched-chain alkylene or hydroxyalkylene radical having up to 7 consecutive carbon atoms in the main chain, and $B'_1$ is a divalent radical which is a straight-chain or branched-chain alkylene radical which has up to 7 consecutive carbon atoms in the main chain, which is unsubstituted or substituted by one or more hydroxyl radicals and which is interrupted by one or more nitrogen atoms, the nitrogen atom being substituted by an alkyl chain which is optionally interrupted by an oxygen atom and which optionally contains one or more hydroxyl groups; these polymers are described in French Pat. No, 2,280,361, incorporated herein by reference;

(iii) polymers that are the alkylation products of the polymers of the formulae (I) and (II) indicated above under (i) and (ii) with alkyl or benzyl halides or lower alkyl tosylates or mesylates, and the oxidation products of these polymers;

(f) Water-soluble crosslinked polyaminopolyamides obtained by crosslinking a polyaminopolyamide comprising at least one water-soluble cross-linked polymer obtained by crosslinking a polyaminopolyamide prepared by the polycondensation of an acid compound, with a polyamine by means of a crosslinking agent chosen from the group comprising:

(I) compounds of the group comprising: (i) bis-halogenohydrins, (ii) bis-azetidinium compounds, (iii) bis-halogenoacyldiamines and (iv) bis (alkyl halides);

(II) oligomers obtained by reacting a compound "a" chosen from the group comprising: (i) bis-halogenohydrins, (ii) bis-azetidinium compounds, (iii) bis-halogenoacyldiarnines, (iv) bis(alkyl halides), (v) epihalogenohydrins, (vi) diepoxides and (vii) bis-unsaturated derivatives, with a compound 'b' which is a difuntional compound reactive towards the compound "a"; and (III) the quaternisation product of a compound chosen from the group comprising the compounds (I) mentioned above and the obligomers (II) and containing one or more tertiary amine groups which can be totally or partially alkylated with an alkylating agent (c) preferably chosen from the group comprising methyl or ethyl chlorides, bromides, iodides, sulphates, mesylates and tosylates, benzyl chloride or bromide, ethylene oxide, propylene oxide and glycerol. These crosslinking agents and these polymers are described in French Pat. No. 2,368,508, incorporated herein by reference.

(g) Polyaminopolyamide derivatives resulting from the condensation of polyalkylene-polyamines with polycarboxylic acids, followed by akylation with difunctional agents. Examples which may be mentioned are adipic acid/dialkylaminohydroxyalkyl-dialkylenetriamine polymers in which the alkyl radical contains from 10 to 4 carbon atoms and preferably denotes methyl, ethyl or propyl, which are described in French Pat. No. 1,583,363 (incorporated herein by reference), and which include adipic acid/dimethylaminohydroxypropyl-diethylenetriamine polymers sold under the same Cartaretine F, $F_4$ or $F_8$ by Sandoz Chemicals.

(h) the products listed under the names Quaternium 38, 37, 49 and 42 in the Cosmetic Ingredient Dictionary; the acrylamide/beta-methacryloyloxyethyltrimethylammonium methosulphate copolymers sold under the names Reten 205, 210, 220 and 240 by Hercules; the aminoethylserylate phosphate/acrylate copolymer sold under the name Catrex by National Starch (Bridgewater, N.J.); and graft crosslinked cationic copolymers having a molecular weight of 10,000 to 1,000,000 and preferably of 15,000 to 500,000, resulting from the copolymeristion of (a) at least one cosmetic monomer, (b) dimethylaminosthyl methacrylate, (c) polyethylene glycol and (d) a polyunsaturated crosslinking agent, these copolymers being described in French Pat. No. 2,189,434.

(i) Quaternary vinylpyrrolidone/vinylimidazole polymers such as, for example, Luviquat FC905 sold by BASF Corporation (Mt. Olive, N.J.).

(j) Cationic silicone polymers, for example those described in European Applications 17,121 and 17,122, U.S. Pat. No. 4,185,087, Japanese Patent Application No. 80 66,506 and Austrian Patent Application 71/01,171 or those mentioned in the CTFA dictionary under the name AMODIMETHICONE such as the product marketed as a mixture with other ingredients under the name "Dow Corning 929" cationic emulsion (Dow Coming, Midland, Mich.).

(k) polyalkyleneimines, in particular polyethyleneimines, polymers containing vinylpyridine units or vinylpyridinium units in the chain, condensates of polyamines and epichlorohydrin, poly(quaternary ureylene) compounds and chiten derivatives.

(l) Quaternary polyvinylpyrrolidone copolymer having a molecular weight of 100,000, for example, the polymer sold under the tradename GAFQUAT 734 by International Specialty Products (Boundbrook, N.J.);

(m) Vinyl acetate/crotonic acid copolymers, for example the polymer sold by Hoechst Celanese Corp. (Charlotte, N.C.) under the name ARISTOFLEX A.

(n) Quaternary polyvinylpyrrolidone copolymers having a molecular weight of 1,000,000, such as that sold by International Specialty Products (Boundbrook, N.J.) under the name GAFQUAT 755.

(o) Quaternary polyvinylpyrrolidone copolymer having a molecular weight of 100,000, such as that sold by International Specialty Products (Boundbrook, N.J.) GAFQUAT 734.

(p) Vinylpyrrolidone/methylvinylimidazolinium chloride copolymers, such as that sold as a 40% aqueous solution under the same LUVIQUAT FC 905 by BASF.

Some examples of nonionic polymers which may be used according to the invention include, but are not limited to, DATEM (commercially available under the trade name Amilan® GST 40 from Goldschmidt Chemical Corporation, Hopewell, Va.); PEG-18 glyceryl oleate/cocoate (commercially available under the trade name Antil® 171, from Goldschmidt Chemical Corporation, Hopewell, Va.) and glyceryl laurate (commercially available under the trade name Tegin™ L-90, from Goldschmidt Chemical Corporation (Hopewell, Va.).

The preferred polymers of the invention include polyquaternium-10, polyquaternium-4 and the polymer that is the product of a condensation reaction of ethylenediamine, dimethylamine and epichlorohydrin.

The quaternary ammonium compounds which can be used according to the present invention include (but are not limited to) cationic acrylamide copolymer salts, for example, the dimethyldiallylammonium chloride homopolymer sold under the name MERQUAT 100 (commercially available from Merck Laboratories, Whitehouse Station, N.J.), the dimethyldiallylammonium chloride acrylamide compound which is sold under the name MERQUAT 550 (commercially available from Merck Laboratories, Whitehouse Station, N.J.), the cationic acrylamide copolymer salt sold under the name Polytec 65 (Polytec, Incorporated, Gulf Shores, Ala.); isostearyl ethylimidonium ethosulfate (commercially available under the trade name Monoquat ISIES™, from Mona Industries, Paterson, N.J.) and cetrimonium chloride, commercially available under the trade name Barquat™ CT-29 from Lonza, Inc., Fairlawn, N.J.

The hair processing compositions of the invention are any commercially available hair processing product, including but not limited to relaxers, permanent waving compositions, dyes and bleaches. For example, one such product, relaxers, typically contain either guanidine hydroxide, sodium hydroxide, potassium hydroxide, lithium hydroxide, thioglycollate or quaternary ammonium hydroxide as the active hair-relaxing ingredient. One such suitable relaxing product is AFFIRM Creme Relaxer, available from Avlon Industries, Inc., Chicago, Ill. Other relaxing cremes and methods of relaxing hair are disclosed in U.S. Pat. Nos. 5,068,101, 5,068,680 and 5,148,822 to Akhtar et al., which are incorporated herein by reference. The permanent waving compositions of the invention include any commercially available preparation, for example, FERM® (commercially available from Avlon Industries, Inc., Chicago, Ill.). The permanent coloring compositions of the invention include any commercially available permanent colorant, for example, those sold under the tradename Complements™, by Clairol, Inc. (Stamford, Conn.).

The preferred embodiment of the composition of the present invention comprises (a) at least one cationic or polar non-ionic polymer; and at least one (b) sugar, starch hydrolysate, sorbitol, glycerol, propylene glycol or a polyol; and (c) a quaternary ammonium compound; and various pH adjusting and conditioning agents. Preferable ranges for the preferred components of an embodiment of the composition of the present invention utilizing sucrose are set forth in Table 1:

TABLE 1

| MATERIAL | QUANTITIES INTRODUCED (approximate range of parts by weight in % of whole) |
| --- | --- |
| Deionized Water | QS*/100 |
| Cationic acrylamide copolymer salt | 0.02–5.0 |
| Polyquaternium-10 | 0.1–10.0 |
| Sucrose | 5–70 |
| Panthenol | 0.1–5.0 |
| Lactic Acid | 1.0–10.0 |
| Sodium Lactate | 1.0–10.0 |
| Quaternary Ammonium Compound | 1.0–20.0 |
| PCA | 0.1–5.0 |
| Solan | 0.1–5.0 |
| Hydrolyzed Protein | 0.25–5.0 |
| Preservatives, fragrance | QS |

*"quantity suitable"

"Cationic acrylamide copolymer salt" is designated by the trade name Polytec 65 and is supplied by Polytec Incorporated, P.O. Box 1247, Gulf Shores, Ala. 36547. "Polyquaternium-10" is designated by the trade name Polymer JR-30M and is supplied by Amerchol Corporation, 136 Talmadge Road, Edison, N.J. 08818. A suitable quaternary ammonium compound is sold under the trade name Carsoquat CT-429 by Lonza, Inc., 17—17 Route 208, Fair Lawn, Ohio 07410. Suitable hydrolyzed proteins are sold under the trade names Hydrolyzed Wheat Protein and Wheat Oligosaccharides, available from Croda, Inc., 7 Century Drive, Parsippany, N.J. 07054.

Preferable ranges for the preferred components of an embodiment of the composition of the present invention utilizing starch hydrolysate are set forth in Table 2:

TABLE 2

| MATERIAL | QUANTITIES INTRODUCED (approximate range of parts by weight in % of whole) |
| --- | --- |
| Deionized Water | QS*/100 |
| Cationic acrylamide copolymer salt | 0.02–5.0 |
| Polyquaternium-10 | 0.1–10.0 |
| Starch hydrolysate | 6.5–91.0 |
| Panthenol | 0.1–5.0 |
| Lactic Acid | 1.0–10.0 |
| Sodium Lactate | 1.0–10.0 |
| Quaternary Ammonium Compound | 1.0–20.0 |
| PCA | 0.1–5.0 |
| Solan | 0.1–5.0 |
| Hydrolyzed Protein | 0.25–5.0 |
| Preservatives, fragrance | QS |

*"quantity suitable"

"Cationic acrylamide copolymer salt" is designated by the trade name Polytec 65 and is supplied by Polytec Incorporated, P.O. Box 1247, Gulf Shores, Ala. 36547. "Polyquaternium-10" is designated by the trade name Polymer JR-30M and is supplied by Amerchol Corporation, 136 Talmadge Road, Edison, N.J. 08818. A suitable starch hydrolysate is Hystar CG, sold by Lonza Inc. (Fairlawn, N.J.). A suitable quaternary ammonium compound is sold under the trade name Carsoquat CT-429 by Lonza, Inc., 17—17 Route 208, Fair Lawn, Ohio 07410. Suitable hydrolyzed proteins are sold under the trade names Hydrolyzed Wheat Protein and Wheat Oligosaccharides, available from Croda, Inc., 7 Century Drive, Parsippany, N.J. 07054.

Surprisingly, the inventors have discovered that the addition of a sugar or starch hydrolysate to compositions comprising polymers known in the art results in a protectorant composition which is a significant improvement over the prior art compositions for protecting previously chemically treated hair during subsequent processing. This result is particularly surprising since many such polymer compositions are used in conjunction with permanent waving compositions, relaxers or hair dyes, and do not inhibit the chemical processes. Examples of polymer-containing conditioning relaxers are disclosed in U.S. Pat. Nos. 5,068,680 and 5,148,822 to Akhtar et al., and examples of conditioning dyes are disclosed in U.S. Pat. No. 4,362,528 to Grollier et al. Thus, it is logical to assume that polymers would not be an effective ingredient in the hair protectorant compounds of the invention.

In addition to the embodiments set forth in Tables I and II, the following embodiments further exemplify the composition of the protectorant composition of the present invention. The following embodiments are provided by way of example only, and are not intended to be limitations.

EXAMPLE 1

| MATERIAL | QUANTITIES INTRODUCED (parts by weight in % of whole) |
| --- | --- |
| Deionized Water | QS/100 |
| Cationic acrylamide copolymer salt | 0.10 |
| Polyquaternium-10 | 0.90 |
| Sucrose | 27.25 |
| Quaternary Ammonium Compound | 3.60 |
| PEG-75 Lanolin | 0.30 |
| Preservatives, fragrance | QS |
| Lactic Acid | 5.00 |
| Sodium Lactate | 6.20 |

To prepare the composition, cationic acrylamide copolymer salt and polyquaternium-10 were dispersed in water at room temperature with a T-Line Laboratory Stirrer manufactured by Talboys Engineering Corp., Montrose, Pa. The mixture was heated to 45° C. Sucrose, quaternary ammonium compound Carsoquat CT-429, PEG-75 Lanolin, preservatives and fragrance were then added to the mixture. The mixture was mixed for 30 minutes until homogenous. The mixture was then cooled to room temperature. The pH was adjusted with lactic acid and sodium lactate. Lactic acid is used as the primary pH-reducing agent as well as for its moisturizing properties.

This composition is applied to previously processed hair prior to further processing.

EXAMPLE 2

| MATERIAL | QUANTITIES INTRODUCED (parts by weight in % of whole) |
| --- | --- |
| Deionized Water | 33.35 |
| Polyquaternium-10 | 0.90 |
| Sucrose | 50.00 |
| Quaternary Ammonium Compound | 3.60 |
| PEG-75 Lanolin | 0.30 |
| Preservatives, fragrance | 0.65 |
| Lactic Acid | 5.00 |
| Sodium Lactate | 6.20 |

The composition is prepared and used as set forth in Example 1.

EXAMPLE 3

| MATERIAL | QUANTITIES INTRODUCED (parts by weight in % of whole) |
| --- | --- |
| Deionized Water | QS/100 |
| Polyquaternium-10 | 0.90 |
| Sucrose | 5.00 |
| Quaternary Ammonium Compound | 3.60 |
| PEG-75 Lanolin | 0.30 |
| Preservatives, fragrance | QS |
| Lactic Acid | 5.00 |
| Sodium Lactate | 6.20 |

The composition is prepared and used as set forth in Example 1.

EXAMPLE 4

| MATERIAL | QUANTITIES INTRODUCED (parts by weight) |
| --- | --- |
| Deionized Water | QS/100 |
| Polyquaternium-10 | 0.90 |
| Fructose | 27.25 |
| Quaternary Ammonium Compound | 3.60 |
| PEG-75 Lanolin | 0.30 |
| Preservatives, fragrance | QS |
| Lactic Acid | 5.00 |
| Sodium Lactate | 6.20 |

The composition was prepared as set forth in Example 1.

EXAMPLE 5

| MATERIAL | QUANTITIES INTRODUCED (parts by weight) |
| --- | --- |
| Deionized Water | QS/100 |
| Polyquaternium-10 | 0.90 |
| Lactose | 27.25 |
| Quaternary Ammonium Compound | 3.60 |
| PEG-75 Lanolin | 0.30 |
| Preservatives, fragrance | QS |
| Lactic Acid | 5.00 |
| Sodium Lactate | 6.20 |

The composition is prepared and used as set forth in Example 1.

EXAMPLE 6

| MATERIAL | QUANTITIES INTRODUCED (parts by weight) |
| --- | --- |
| Deionized Water | QS/100 |
| Polyquaternium-4 | 0.10 |
| Polyquaternium-10 | 0.90 |
| Sucrose | 27.25 |
| Quaternary Ammonium Compound | 3.50 |
| PEG-75 Lanolin | 0.30 |
| Preservatives, fragrance | QS |
| Lactic Acid | 5.00 |
| Sodium Lactate | 6.20 |

The composition is prepared and used as set forth in Example 1, except that polyquaternium-4 was dispersed in the same manner as the polyquaternium-10.

EXAMPLE 7

| MATERIAL | QUANTITIES INTRODUCED (parts by weight) |
| --- | --- |
| Deionized Water | QS/100 |
| Polyquaternium-10 | 0.90 |
| Sucrose | 27.50 |
| Cationic acrylamide copolymer salt | 1.0 |
| PEG-75 Lanolin | 0.30 |
| Preservatives, fragrance | QS |

To prepare the composition, polyquaternium-10 and the cationic acrylamide copolymer salt were dispersed in water at room temperature with a T-Line Laboratory Stirrer manufactured by Talboys Engineering Corp., Montrose, Pa. The mixture was heated to 45° C. Sucrose, Carsoquat CT-429, PEG-75 Lanolin, preservatives and fragrance were then added to the mixture. The mixture was mixed for 30 minutes until homogenous. The mixture was then cooled to room temperature.

The composition is used as set forth in Example 1.

EXAMPLE 8

| MATERIAL | QUANTITIES INTRODUCED (parts by weight in % of whole) |
| --- | --- |
| Deionized Water | QS/100 |
| Betz ® Polymer 1195 | 1.8 |
| Sucrose | 27.50 |
| Quaternary Ammonium Compound | 3.60 |
| PEG-75 Lanolin | 0.30 |
| Preservatives, fragrance | QS |
| Lactic Acid | 5.00 |
| Sodium Lactate | 6.20 |

The composition is prepared and used as set forth in Example 1.

The process of the present invention is suitable for use on hair which has been previously chemically treated, such as (but not limited to) by the process of lanthionization, including but not limited to lanthionization using a non-reducing base such as sodium hydroxide, guanidine hydroxide, potassium hydroxide, lithium hydroxide or quaternary ammonium hydroxide as the active hair-relaxing ingredient; or by permanent waving, or by bleaching or permanent coloring.

A preferred embodiment of the process of the present invention includes a thorough application of the protectorant compositions of the invention to hair which has been previously relaxed. Great care is taken not to apply this product to new growth of hair that needs to be relaxed. After application of a composition of the invention, the hair is chemically treated by relaxing in the second step of the process of the invention, by applying a relaxing agent for a time sufficient to achieve the desired results. Any commercially-available relaxing agent may be used for this step. Such relaxing agents and methods of relaxing are disclosed in U.S. Pat. No. 5,068,101 to Akhtar, and are incorporated herein by reference. The third step involves rinsing the solution and normalizing the hair with a mild shampoo with a pH in the range of 4.0 to 6.0 to stop the action of the relaxer and neutralize any residual active ingredients on the surface of the hair fibers. This process differs from conventional relaxing processes in that in the conventional processes, the previously chemically treated hair is not protected from the relaxer during touchups by applying the compositions of the invention.

Other embodiments of the process of the present invention include the process as described above, utilizing bleaching compositions, permanent waving compositions and coloring compositions as the processing composition of the invention, instead of the relaxing composition described above. Other embodiments include compositions for processing hair by relaxing, bleaching, coloring and permanent waving while protecting previously processed hair, and kits which comprise the compositions of the invention.

To establish that the compositions and processes of the present invention protects the hair from damage during lanthionization, tensile strength studies were performed. These studies involved comparing the tensile strength of relaxed hair fibers which had been relaxed twice using the conventional method, versus hair fibers treated by the process and composition of the present invention prior to the second application of the relaxer. The conventional process involved treating hair fibers twice with a relaxing cream to simulate the overlap of relaxer on previously chemically treated hair which occurs during touch-ups. The process and composition of the present invention involved treating hair fibers once with relaxer cream as in the conventional method, followed by application of the composition of the present invention, which was then followed by the second relaxer application. For the conventional method, the tresses were treated by applying a conventional relaxing cream to the whole length of the hair fibers for 18 minutes. After the processing time was complete, the tress was rinsed thoroughly with warm tap water and shampooed with a non-conditioning shampoo. The tress was allowed to dry overnight in an environmentally controlled room at 21° C. and 65% relative humidity.

For the second treatment, the same tresses as above were divided in half and the bottom portion (towards the ends) was treated with the composition of the present invention prior to the second application of cream relaxer. The upper portion (closest to the roots) of the tress was not treated with this composition. The tresses were again treated with relaxing cream along the whole length of the fibers for 18 minutes, rinsed and shampooed.

Following the second treatment, the tresses were allowed to dry overnight in an environmentally controlled room at 21° C. and 65% relative humidity. After drying, fibers were tested for tensile strength using a Dia-Stron Miniature Tensile Tester manufactured by Dia-Stron Limited of the United Kingdom. The tensile strength was determined by establishing the amount of work required to extend the hair fibers to 20 percent of their original length (F20) as well as the work required to break the fibers.

The statistical significance of the results were obtained by using the Student t-test. These results establish that the fibers which were treated with the composition and process of the present invention were significantly stronger than fibers treated twice using the conventional method. These results are set forth in Tables 3 and 4.

TABLE 3

WORK REQUIRED FOR 20% ELONGATION

| Hair Fiber # | Fibers Relaxed Twice Using Conventional Process | Fibers Relaxed Twice by Process/Composition of Present Invention |
|---|---|---|
| 1 | 0.98 | 1.17 |
| 2 | 0.84 | 0.94 |
| 3 | 0.88 | 1.18 |
| 4 | 0.98 | 1.48 |
| 5 | 0.87 | 1.12 |
| 6 | 1.07 | 1.06 |
| 7 | 1.02 | 1.06 |
| 8 | 1.10 | 1.24 |
| 9 | 0.64 | 0.89 |
| 10 | 1.03 | 1.71 |
| 11 | 0.92 | 0.98 |
| 12 | 0.83 | 1.24 |
| 13 | 1.17 | 1.61 |
| 14 | 1.33 | 1.11 |
| 15 | 1.03 | 1.23 |
| 16 | 1.03 | 1.23 |
| 17 | 0.99 | 1.28 |
| 18 | 0.93 | 1.30 |
| 19 | 1.18 | 1.57 |
| 20 | 1.33 | 0.97 |
| 21 | 1.34 | 1.12 |
| 22 | 0.92 | 1.16 |
| 23 | 0.91 | 1.11 |
| 24 | 1.07 | 1.47 |
| 25 | 1.02 | 1.31 |
| 26 | 0.95 | 1.08 |
| 27 | 1.23 | 1.28 |
| 28 | 0.87 | 1.23 |
| 29 | 0.85 | 1.34 |
| Average | 1.01 | 1.22 |
| Standard Deviation | 0.16 | 0.20 |

*Work is expressed in millijoules.

Statistical Analysis of the Results

| | |
|---|---|
| n1 | 29 |
| n2 | 29 |
| X1 | 1.01 |
| X2 | 1.22 |
| S.D.1 | 0.16 |
| S.D.2 | 0.20 |
| SD | 0.181 |
| t** | −4.415 |
| | (99.9% Confidence level) |

**Student t-Test of Work of F-20

TABLE 4

WORK* REQUIRED FOR BREAKING HAIR FIBERS

| Hair Fiber # | Fibers Relaxed Twice Using Conventional Process | Fibers Relaxed Twice by Process/Composition of Present Invention |
|---|---|---|
| 1 | 6.82 | 7.13 |
| 2 | 4.91 | 6.10 |
| 3 | 7.15 | 9.88 |
| 4 | 8.43 | 9.72 |
| 5 | 6.18 | 9.27 |
| 6 | 6.67 | 7.38 |
| 7 | 6.45 | 7.25 |
| 8 | 3.45 | 7.20 |
| 9 | 5.33 | 5.62 |
| 10 | 5.84 | 14.50 |
| 11 | 7.69 | 10.50 |
| 12 | 9.27 | 13.30 |
| 13 | 9.83 | 9.70 |
| 14 | 10.10 | 6.11 |

TABLE 4-continued

WORK* REQUIRED FOR BREAKING HAIR FIBERS

| | | |
|---|---|---|
| 15 | 9.29 | 11.00 |
| 16 | 7.19 | 8.57 |
| 17 | 8.18 | 9.15 |
| 18 | 9.19 | 14.80 |
| 19 | 9.18 | 9.55 |
| 20 | 9.54 | 5.18 |
| 21 | 10.60 | 7.14 |
| 22 | 6.32 | 6.99 |
| 23 | 4.46 | 8.86 |
| 24 | 7.45 | 12.90 |
| 25 | 11.80 | 9.64 |
| 26 | 5.87 | 8.48 |
| 27 | 9.06 | 11.70 |
| 28 | 6.87 | 9.41 |
| 29 | 5.99 | 10.80 |
| Average | 7.56 | 9.24 |
| Standard Deviation | 1.99 | 2.53 |

*Work is expressed in millijoules.
Statistical Analysis of the Results

| | |
|---|---|
| n1 | 29 |
| n2 | 29 |
| X1 | 7.56 |
| X2 | 9.24 |
| S.D.1 | 1.99 |
| S.D.2 | 2.63 |
| SD | 2.332 |
| t** | −2.743 |
| | (95.0% Confidence level) |

**Student t-Test of Break Work

Studies have also shown that sugar solutions without a cationic polymer do not protect previously chemically treated hair from relaxer damage. Results of experiments comparing the tensile strength of fibers treated twice with a relaxing cream with fibers treated with a composition containing 27.5% of a sugar suitable for use in the composition of the method, 5.00% Lactic acid, and 6.20% Sodium lactate prior to the second relaxing process are set forth in Tables 5 and 6.

The results indicate that the difference in tensile strength of hair between treatments used to generate the data in Tables 5 and 6 is statistically insignificant (using the Student t-test).

TABLE 5

WORK* REQUIRED FOR 20% ELONGATION

| Hair Fiber # | Fibers Relaxed Twice Using Conventional Process | Fibers Relaxed Twice by Process/Composition without Polymers |
|---|---|---|
| 1 | 1.12 | 1.07 |
| 2 | 1.30 | 1.00 |
| 3 | 1.33 | 1.13 |
| 4 | 1.27 | 1.20 |
| 5 | 0.79 | 0.63 |
| 6 | 1.25 | 0.97 |
| 7 | 1.45 | 1.50 |
| 8 | 1.48 | 1.25 |
| 9 | 1.07 | 0.91 |
| 10 | 1.16 | 0.99 |
| 11 | 1.46 | 1.32 |
| 12 | 1.18 | 1.26 |
| 13 | 1.20 | 1.17 |
| 14 | 1.14 | 1.36 |
| 15 | 0.98 | 1.02 |
| 16 | 1.39 | 1.54 |
| 17 | 0.86 | 1.06 |
| 18 | 1.19 | 0.99 |
| 19 | 1.23 | 1.21 |
| 20 | 1.19 | 1.03 |
| 21 | 1.04 | 0.85 |
| 22 | 1.16 | 1.42 |
| 23 | 1.62 | 1.78 |
| 24 | 1.20 | 1.12 |
| 25 | 1.12 | 0.93 |
| 26 | 1.15 | 1.30 |
| 27 | 1.00 | 1.15 |
| 28 | 0.77 | 0.63 |
| 29 | 1.30 | 1.30 |
| 30 | 1.23 | 1.42 |
| Average | 1.19 | 1.15 |
| Standard Deviation | 0.19 | 0.25 |

*Work is expressed in millijoules.
Statistical Analysis of the Results

| | |
|---|---|
| n1 | 30 |
| n2 | 30 |
| X1 | 1.19 |
| X2 | 1.15 |
| S.D.1 | 0.19 |
| S.D.2 | 0.25 |
| SD | 0.222 |
| t** | 0.698 |
| | (Less than 80% confidence) |

**Student t-Test of Area of F-20

TABLE 6

WORK* REQUIRED FOR BREAKING HAIR FIBERS

| Hair Fiber # | Fibers Relaxed Twice Using Conventional Process | Fibers Relaxed Twice by Process/Composition without polymers |
|---|---|---|
| 1 | 8.55 | 8.21 |
| 2 | 9.22 | 6.77 |
| 3 | 4.38 | 4.98 |
| 4 | 9.64 | 7.07 |
| 5 | 11.10 | 10.80 |
| 6 | 9.40 | 8.07 |
| 7 | 8.96 | 7.86 |
| 8 | 8.41 | 6.79 |
| 9 | 11.50 | 9.68 |
| 10 | 8.08 | 9.03 |
| 11 | 7.33 | 8.00 |
| 12 | 8.56 | 9.07 |
| 13 | 9.44 | 12.90 |
| 14 | 6.19 | 6.09 |
| 15 | 9.35 | 10.50 |
| 16 | 5.74 | 7.21 |
| 17 | 6.20 | 7.46 |
| 18 | 9.59 | 7.85 |
| 19 | 9.24 | 9.95 |
| 20 | 7.83 | 6.60 |
| 21 | 8.12 | 9.52 |
| 22 | 11.00 | 9.94 |
| 23 | 8.56 | 7.34 |
| 24 | 6.00 | 5.56 |
| 25 | 7.30 | 8.57 |
| 26 | 7.34 | 7.21 |
| 27 | 6.59 | 5.13 |
| 28 | 9.50 | 10.40 |
| 29 | 7.06 | 8.47 |
| 30 | 9.77 | 9.52 |
| Average | 8.33 | 8.22 |
| | 1.68 | 1.81 |

*Work is expressed in millijoules.
Statistical Analysis of the Results

| | |
|---|---|
| n1 | 30 |
| n2 | 30 |

TABLE 6-continued

WORK* REQUIRED FOR BREAKING HAIR FIBERS

| | |
|---|---|
| X1 | 8.33 |
| X2 | 8.22 |
| S.D.1 | 1.68 |
| S.D.2 | 1.81 |
| SD | 1.75 |
| t** | 0.244 |
| | (Less than 80% confidence) |

**Student t-Test of Area of Break Force

Compositions containing a cationic acrylamide copolymer salt and a cationic polymer without sugar were also ineffective at protecting previously chemically treated hair during subsequent relaxation of the new hair growth. Results of experiments comparing the tensile strength of fibers treated twice with a relaxing cream with fibers treated with a composition containing with 0.10% cationic acrylamide copolymer salt and 0.90% cationic polymer in solution containing 5.00% lactic acid, 6.20% sodium lactate in the absence of sugar are set forth in Tables 7 and 8. The results shown in Tables 7 and 8 (polymer without sugar) are statistically insignificant, as analyzed using the Student t-test.

TABLE 7

WORK* REQUIRED FOR 20% ELONGATION

| Hair Fiber # | Fibers Relaxed Twice Using Conventional Process | Fibers Relaxed Twice by Process/Composition without Sucrose |
|---|---|---|
| 1 | 0.86 | 1.02 |
| 2 | 0.99 | 0.82 |
| 3 | 1.21 | 1.30 |
| 4 | 0.73 | 0.82 |
| 5 | 0.98 | 0.73 |
| 6 | 0.79 | 0.96 |
| 7 | 1.04 | 0.90 |
| 8 | 1.24 | 1.34 |
| 9 | 0.78 | 1.07 |
| 10 | 1.01 | 0.98 |
| 11 | 1.04 | 1.09 |
| 12 | 0.98 | 0.68 |
| 13 | 1.00 | 1.16 |
| 14 | 1.15 | 1.28 |
| 15 | 0.64 | 0.71 |
| 16 | 0.99 | 1.33 |
| 17 | 0.62 | 0.69 |
| 18 | 0.82 | 0.79 |
| 19 | 0.62 | 0.53 |
| 20 | 0.92 | 0.64 |
| 21 | 0.90 | 0.67 |
| 22 | 1.18 | 1.23 |
| 23 | 0.70 | 0.93 |
| 24 | 0.99 | 0.54 |
| 25 | 0.92 | 1.13 |
| 26 | 0.79 | 1.35 |
| 27 | 1.23 | 1.32 |
| 28 | 0.84 | 0.56 |
| 29 | 1.49 | 1.13 |
| 30 | 0.94 | 0.72 |
| Average | 0.95 | 0.95 |
| Standard Deviation | 0.20 | 0.27 |

*Work is expressed in millijoules.
Statistical Analysis of the Results

| | |
|---|---|
| n1 | 30 |
| n2 | 30 |
| X1 | 0.95 |
| X2 | 0.95 |
| S.D.1 | 0.20 |

TABLE 7-continued

WORK* REQUIRED FOR 20% ELONGATION

| | |
|---|---|
| S.D.2 | 0.27 |
| SD | 0.24 |
| t** | −0.011 |
| | (Less than 80% confidence) |

**Student t-Test of Area of F-20

TABLE 8

WORK* REQUIRED FOR BREAKING HAIR FIBERS

| Half Fiber # | Fibers Relaxed Twice Using Conventional Process | Fibers Relaxed Twice by Process/Composition without Sucrose |
|---|---|---|
| 1 | 6.67 | 7.00 |
| 2 | 7.29 | 4.97 |
| 3 | 12.50 | 9.80 |
| 4 | 7.97 | 5.82 |
| 5 | 7.10 | 8.37 |
| 6 | 6.16 | 7.84 |
| 7 | 8.18 | 8.21 |
| 8 | 11.00 | 10.80 |
| 9 | 5.31 | 8.38 |
| 10 | 7.01 | 4.78 |
| 11 | 8.29 | 7.83 |
| 12 | 7.37 | 4.56 |
| 13 | 7.29 | 8.84 |
| 14 | 9.08 | 8.49 |
| 15 | 5.54 | 6.54 |
| 16 | 6.49 | 8.83 |
| 17 | 3.33 | 4.70 |
| 18 | 3.67 | 4.92 |
| 19 | 5.04 | 2.04 |
| 20 | 9.11 | 5.42 |
| 21 | 7.80 | 5.63 |
| 22 | 9.07 | 9.33 |
| 23 | 7.55 | 8.51 |
| 24 | 8.83 | 3.42 |
| 25 | 8.77 | 10.10 |
| 26 | 8.05 | 10.40 |
| 27 | 6.84 | 12.10 |
| 28 | 5.79 | 6.19 |
| 29 | 12.80 | 8.92 |
| 30 | 6.40 | 4.30 |
| Average | 7.54 | 7.23 |
| Standard Deviation | 2.14 | 2.43 |

*Work is expressed in millijoules.
Statistical Analysis of Results

| | |
|---|---|
| n1 | 30 |
| n2 | 30 |
| X1 | 7.54 |
| X2 | 7.23 |
| S.D.1 | 2.14 |
| S.D.2 | 2.43 |
| SD | 2.29 |
| t** | 0.524 |
| | (Less than 80% confidence) |

**Student t-Test of Break Work

The surprising results shown in tables 3 through 8 above indicate that the combination of at least one sugar and at least one cationic polymer of the invention have an unexpected and synergistic effect in blocking the damaging effects of the chemical used to process the hair, in this case a relaxing composition. It is believed that the polymer helps to affix the sugar to the hair shaft, rendering the sugar effective in blocking the action of the processing compositions. The pH-reducing agent in the composition is used to help neutralize the relaxing cream, which may retard the lanthionization process in the hair fiber. However, compositions containing the polymers and sugar without the presence of a pH reducing agent have also been shown to be successful in reducing hair damage, as shown by the data displayed in Tables 9 and 10, below. Based upon these surprising results, we conclude that the compositions and methods of the invention are applicable to a wide range of chemical processes, including permanent coloring, bleaching, relaxing and permanent waving.

TABLE 9

WORK* REQUIRED FOR 20% ELONGATION

| Hair Fiber # | Fibers Relaxed Twice Using Conventional Process | Fibers Relaxed Twice by Process/Composition without pH adjustment |
|---|---|---|
| 1 | 1.11 | 1.23 |
| 2 | 0.97 | 1.32 |
| 3 | 1.04 | 1.18 |
| 4 | 0.90 | 0.93 |
| 5 | 1.02 | 1.28 |
| 6 | 0.72 | 1.01 |
| 7 | 0.78 | 1.02 |
| 8 | 1.00 | 1.25 |
| 11 | 1.28 | 1.25 |
| 12. | 1.01 | 0.92 |
| 13 | 0.92 | 1.10 |
| 14 | 0.97 | 1.02 |
| 15 | 0.96 | 1.43 |
| 16 | 0.70 | 0.69 |
| 18 | 1.19 | 1.30 |
| 20 | 0.79 | 0.85 |
| 21 | 0.87 | 1.17 |
| 22 | 1.10 | 0.89 |
| 23 | 0.78 | 1.06 |
| 24 | 0.89 | 0.87 |
| 25 | 1.01 | 0.85 |
| 26 | 0.95 | 1.41 |
| 27 | 1.14 | 1.33 |
| 28 | 1.20 | 1.62 |
| 29 | 0.90 | 0.74 |
| 30 | 0.83 | 0.82 |
| 31 | 1.10 | 0.99 |
| 32 | 0.85 | 1.05 |
| 33 | 0.76 | 1.10 |
| 35 | 0.83 | 0.92 |
| AVERAGE | 0.952 | 1.086 |
| sd | 0.150 | 0.224 |

*Work is expressed in millijoules.

Statistical Analysis of Results

| n1 | 30.00 |
| n2 | 30.00 |
| X1 | 0.96 |
| X2 | 1.09 |
| S.D.1 | 0.15 |
| S.D.2 | 0.22 |
| SD | 0.19 |
| t** | −2.66 |
| | (95% Confidence level) |

**Student t-Test of Area of F-20

TABLE 10

WORK REQUIRED FOR BREAKING HAIR FIBERS

| | Fibers Relaxed Twice Using Conventional Process | Fibers Relaxed Twice by Process/Composition without pH adjustment |
|---|---|---|
| 1 | 9.59 | 9.38 |
| 2 | 8.83 | 10.10 |
| 3 | 12.30 | 9.03 |
| 4 | 7.82 | 8.70 |
| 5 | 8.62 | 9.55 |
| 6 | 8.45 | 9.58 |
| 7 | 6.46 | 7.34 |

TABLE 10-continued

WORK REQUIRED FOR BREAKING HAIR FIBERS

| 8 | 7.96 | 9.71 |
|---|---|---|
| 11 | 12.10 | 9.71 |
| 12 | 7.46 | 5.86 |
| 13 | 9.72 | 8.72 |
| 14 | 9.32 | 8.71 |
| 15 | 8.22 | 10.90 |
| 16 | 6.50 | 6.71 |
| 18 | 13.50 | 9.71 |
| 20 | 5.88 | 5.71 |
| 21 | 8.97 | 9.84 |
| 22 | 7.48 | 6.66 |
| 23 | 6.23 | 5.40 |
| 24 | 9.43 | 7.40 |
| 25 | 10.20 | 6.36 |
| 26 | 8.99 | 11.40 |
| 27 | 9.36 | 11.30 |
| 28 | 11.30 | 12.30 |
| 29 | 7.22 | 6.41 |
| 30 | 8.70 | 9.58 |
| 31 | 8.36 | 7.90 |
| 32 | 5.80 | 8.05 |
| 33 | 6.86 | 9.24 |
| 35 | 6.25 | 7.32 |
| AVERAGE | 8.596 | 8.619 |
| SD | 1.932 | 1.803 |

Statistical Analysis of Results

| n1 | 30.00 |
| n2 | 30.00 |
| X1 | 8.60 |
| X2 | 8.62 |
| S.D.1 | 1.93 |
| S.D.2 | 1.80 |
| SD | 1.87 |
| t** | −0.048 |
| | (Less than 80% Confidence Level) |

**Student T-test of Break Work

In accordance with the invention, we have disclosed a novel composition and method that blocks the relaxing process on previously relaxed hair during subsequent relaxing treatments. It is also hypothesized that the compositions and methods of the invention are effective for use during any subsequent chemical treatment of hair, including but not limited to bleaching, dyeing and permanent waving. Accordingly, the composition and process of the present invention significantly reduces structural damage to the hair during chemical processing, and provides processing methods and compositions for previously chemically treated hair that results in stronger, healthier, and more manageable hair than previously chemically treated hair which is processed without the use of the compositions and methods of the invention.

The present invention has been described with respect to certain embodiments and conditions, which are not meant to and should not be construed to limit the invention. Those skilled in the art will understand that variations from the embodiments and conditions described herein may be made without departing from the spirit and scope of the invention as described in the appended claims.

We claim:

1. A method for protecting previously chemically processed hair during subsequent chemical processing comprising the steps of:
   (a) applying to the previously processed hair a protectorant composition that inhibits further processing comprising:
      (i) at least one component selected from the group consisting of a sugar, a starch hydrolysate, sorbitol, glycerol, propylene glycol, or a polyol; and (ii) at least one cationic or polar, non-ionic polymer; and thereafter (b) chemically processing the hair; and thereafter (c) rinsing the hair for a sufficient time to remove all the chemicals from the hair.

2. The method of claim 1 wherein the step of processing the hair includes the step of relaxing the hair.

3. The method of claim 1 wherein the step of processing the hair fibers includes the step of coloring the hair.

4. The method of claim 1 wherein the step of processing the hair fibers includes the step of bleaching the hair.

5. The method of claim 1 wherein the step of processing the hair fibers includes the step of permanently waving the hair.

6. The method of claim 1 wherein the sugar or starch hydrolysate is selected from the group consisting of mono-, di- and polysaccharides, Hystar CG, Hystar 6075, Hystar HM 75 and Hystar 7000.

7. The method of claim 1 wherein the protectorant composition comprises sucrose, fructose, lactose, Hystar CG, Hystar 6075, Hystar HM 75 and Hystar 7000.

8. The method of claim 1 wherein the sugar or starch hydrolysate is selected from the group consisting of sucrose, fructose or Hystar CG, and at least one cationic polymer is selected from the group consisting of:

(a) polyquaternium-10;

(b) polyquaternium-4; and (c) a cationic polyquaternary polymer that is the product of a condensation reaction of ethylenediamine, dimethylamine and epichlorohydrin;

and the step of processing the hair includes the step of relaxing the hair.

9. The method of claim 1 wherein the protectorant composition further comprises a quaternary ammonium compound.

10. The method of claim 9 wherein the quaternary ammonium compound is a cationic acrylamide copolymer salt.

11. The method of claim 9 wherein the quaternary ammonium compound is selected from the group consisting of dimethyldiallylammonium chloride homopolymers, dimethyldiallylammonium chloride acrylamide copolymers, cationic acrylamide copolymer salts, isostearyl ethylimidonium ethosulfate and cetrimonium chloride.

12. A composition for protecting previously chemically treated hair during subsequent relaxing comprising:

(i) at least one component selected from the group consisting of a sugar, a starch hydrolysate, sorbitol, glycerol, propylene glycol, or a polyol; and (ii) at least one cationic or polar, non-ionic polymer; admixed in a cosmetically acceptable medium.

13. The composition of claim 12 wherein the composition further comprises a quaternary ammonium compound.

14. The composition of claim 12 wherein the sugar or starch hydrolysate is selected from the group consisting of mono-, di- and polysaccharides, Hystar CG, Hystar 6075, Hystar HM 75 and Hystar 7000.

15. The composition of claim 12 wherein the polymer is selected from the group consisting of:

(a) polyquaternium-10;

(b) polyquaternium-4; and (c) a cationic polyquaternary polymer that is the product of a condensation reaction of ethylenediamine, dimethylamine and epichlorohydrin.

16. The composition of claim 12 wherein the composition further comprises a pH reducing agent and the composition has a pH in the range of from about 3.0 to 7.0.

17. The composition of claim 12 wherein the sugar or starch hydrolysate is selected from the group consisting of sucrose, lactose and Hystar CG and the polymer comprises, alone or in combination, polyquaternium-10, polyquaternium-4 and the cationic polyquaternary polymer that is the product of a condensation reaction of ethylenediamine, dimethylamine and epichlorohydrin.

18. The composition of claim 13 wherein the quaternary ammonium compound is selected from the group consisting of dimethyldiallylammonium chloride homopolymers, dimethyldiallylammonium chloride acrylamide copolymers, cationic acrylamide copolymer salts, isostearyl ethylimidonium ethosulfate and cetrimonium chloride.

19. The composition of claim 13 comprising:

(a) between 0.12 and 8.0 parts by weight of a cationic or polar non-ionic polymer;

(b) between about 5.0 and 90.0 parts by weight of a sugar, starch hydrolysate, sorbitol, glycerol, propylene glycol or a polyol;

(c) between about 1.0 and 10.0 parts by weight of a quaternary ammonium compound.

20. A single-use kit for processing previously chemically processed hair comprising the following removably affixed components:

(a) a single-use portion of any composition used for chemically processing hair; and (b) a single-use portion of a composition for protecting previously chemically treated hair during subsequent chemical treatment comprising:

(i) at least one component selected from the group consisting of a sugar; a starch hydrolysate, sorbitol, glycerol, propylene glycol, or a polyol; and (ii) at least one cationic or polar, non-ionic polymer.

21. The kit of claim 20 wherein the composition for chemically processing hair comprises a relaxing composition.

22. The kit of claim 20 wherein the composition for chemically processing hair comprises a bleaching composition.

23. The kit of claim 20 wherein the composition for chemically processing hair comprises a coloring composition.

24. The kit of claim 20 wherein the composition for chemically processing hair comprises a permanent waving composition.

25. The kit of claim 21 further comprising a sugar or starch hydrolysate selected from the group consisting of sucrose, lactose and Hystar CG and the polymer comprises, alone or in combination, polyquaternium-10, polyquaternium-4 and the cationic polyquaternary polymer that is the product of a condensation reaction of ethylenediamine, dimethylamine and epichlorohydrin.

26. The kit of claim 20 further comprising one or more of the following removably affixed components:

(a) gloves (b) a conditioner composition (c) a shampoo.

* * * * *